United States Patent [19]

Chung et al.

[11] Patent Number: 5,686,607
[45] Date of Patent: Nov. 11, 1997

[54] PYRIDYL ETHYLATION OF LACTAM DERIVATIVES

[75] Inventors: John Y. L. Chung, Edison; Dalian Zhao, Fanwood; David J. Mathre, Skillman, all of N.J.

[73] Assignee: Merck & Co., Inc., Rahway, N.J.

[21] Appl. No.: 702,486

[22] PCT Filed: Sep. 16, 1994

[86] PCT No.: PCT/US94/10518

§ 371 Date: Aug. 29, 1996

§ 102(e) Date: Aug. 29, 1996

[87] PCT Pub. No.: WO95/25088

PCT Pub. Date: Sep. 21, 1995

[51] Int. Cl.[6] .................................................. G07D 401/06
[52] U.S. Cl. .................... 540/524; 546/193; 546/281.1; 546/281.4
[58] Field of Search .................... 546/193, 281.1, 546/281.4, 281.2; 540/524

[56] References Cited

U.S. PATENT DOCUMENTS 5,281,585  1/1994  Duggan et al. ............................. 514/79

OTHER PUBLICATIONS

E.E. Mikhlina and M.V. Rubstov, Zh. Obshchei Khim., 1962, 32, 2177–84 (CA(58) 90246.
Shapiro et al., J. Org. Chem., 1962, 27, 174–8.
Leonard et al., J. Med. Chem., 1966, 9, 140.

*Primary Examiner*—Robert T. Bond
*Attorney, Agent, or Firm*—Richard S. Parr; Melvin Winokur

[57] ABSTRACT

The invention is a highly efficient synthesis for making compounds of formula (iv) wherein R is $C_{1-4}$ alkyl or benzyl; and $R^1$, when present, is $C_{1-4}$ alkyl, OH, O—$C_{1-4}$ alkyl, or S—$C_{1-4}$ alkyl; which are useful intermediates for making compounds such as those represented in formula (I).

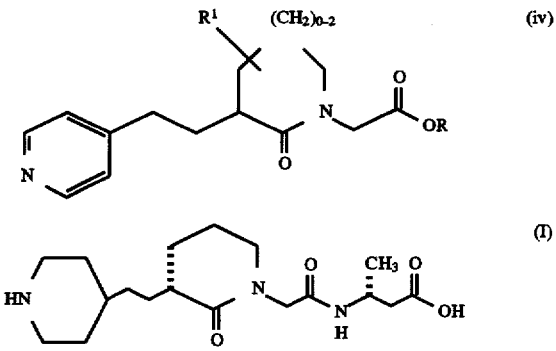

5 Claims, No Drawings

PYRIDYL ETHYLATION OF LACTAM DERIVATIVES

This application is a 371 of PCT/US94/10515, filed 16 Sep., 1994, which claims priority of U.S. Ser. No. 08/212,448 filed 14 Mar., 1994, now abandoned.

BACKGROUND OF THE INVENTION

U.S. Pat. No. 5,281,585, describes fibrinogen receptor antagonists. According to the procedure described in U.S. Pat. No. 5,281,585, the compound:

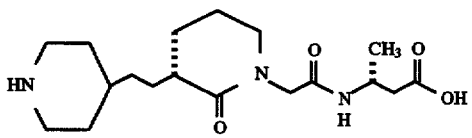

is prepared according to a 17-step procedure which requires the use of expensive reagents and numerous chromatography steps, and gives a <3% overall yield (see columns 63 to 67).

The preparation described in U.S. Pat. No. 5,281,585 involves use of 4-piperidineethanol as a starting material, and a nine step procedure leading to the intermediate

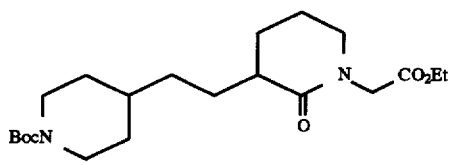

which is thereafter modified to produce various fibrinogen receptor antagonists.

According to the present invention compounds of the formula

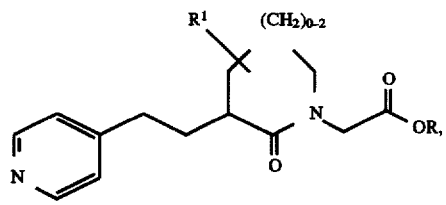

wherein

R is $C_{1-4}$ alkyl or benzyl; and $R^1$, when present, is $C_{1-4}$ alkyl, OH, O—$C_{1-4}$ alkyl, or S—$C_{1-4}$ alkyl;

which are useful as intermediates for preparing numerous fibrinogen receptor antagonists described in U.S. Pat. No. 5,281,585, are prepared according to a three step process using commercially available starting materials.

SUMMARY OF THE INVENTION

The invention includes a process for preparing compounds having the formula

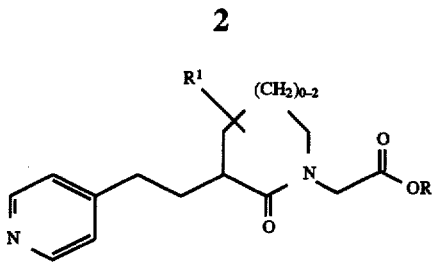

wherein

R is $C_{1-4}$ alkyl or benzyl; and $R^1$, when present, is $C_{1-4}$ alkyl, OH, O—$C_{1-4}$ alkyl, or S—$C_{1-4}$ alkyl;

which comprises a) dissolving a compound having the formula

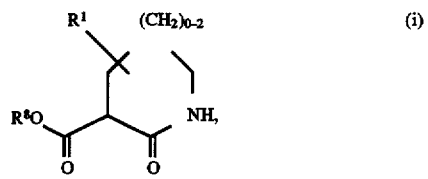
(i)

wherein $R^1$, when present, is $C_{1-4}$ alkyl, OH, O—$C_{1-4}$ alkyl, or S—$C_{1-4}$ alkyl; and $R^8$ is $C_{1-4}$ alkyl;

in an anhydrous alcohol solution comprising 4-vinylpyridine to form

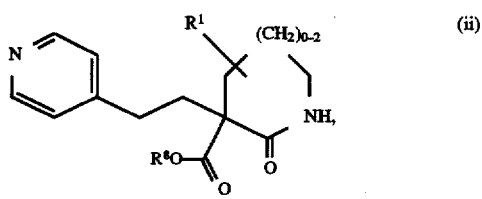
(ii)

b) decarboxylating the compound

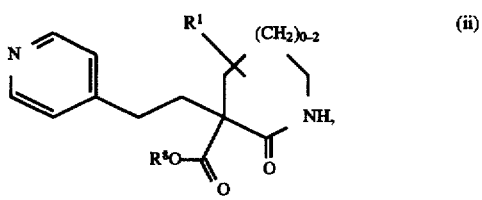
(ii)

to form

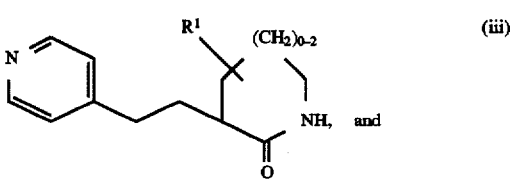
(iii)

c) alkylating iii to form

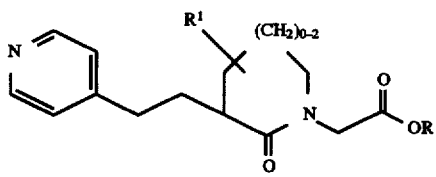

wherein R is $C_{1-4}$ alkyl or benzyl.

When $R^1$ is not present, the compound identified in i is

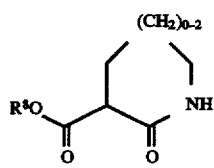

DETAILED DESCRIPTION OF THE INVENTION

The invention includes a process for preparing compounds having the formula

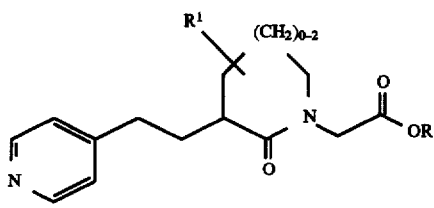

wherein

R is $C_{1-4}$ alkyl or benzyl; and $R^1$, when present, is $C_{1-4}$ alkyl, OH, O—$C_{1-4}$ alkyl, or S—$C_{1-4}$ alkyl;

which comprises a) dissolving a compound having the formula

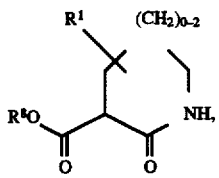

wherein $R^8$ is $C_{1-4}$ alkyl, in an anhydrous alcohol solution comprising 4-vinylpyridine to form

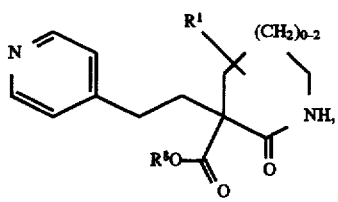

b) decarboxylating the compound

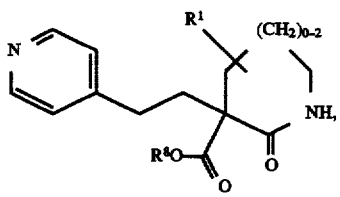

to form

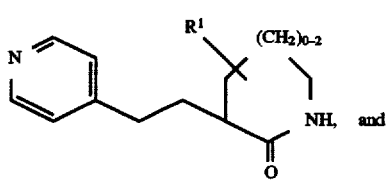

c) alkylating iii to form

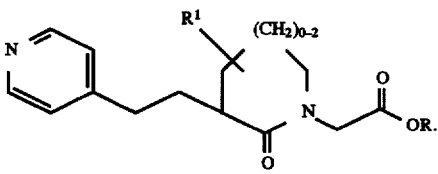

In one embodiment of the process, compound ii is decarboxylated in the presence of aqueous sodium hydroxide.

In another embodiment, compound iii is alkylated in the presence of a strong base, e.g. n-butyllithium.

In another embodiment, the process involves preparing a compound having the formula

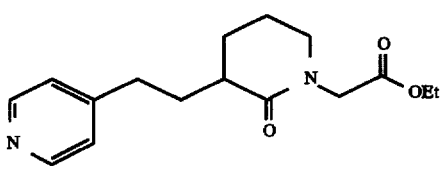

which comprises a) dissolving a compound having the formula

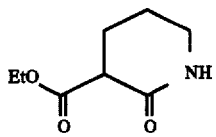

in an anhydrous alcohol solution comprising 4-vinylpyridine to form

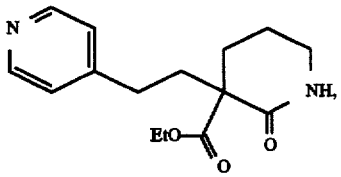

b) decarboxylating the compound

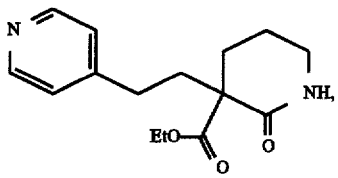
(ii-a)

to form

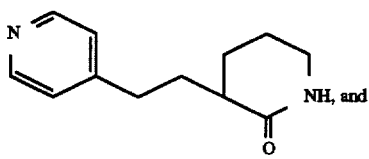
(iii-a)

c) alkylating iii to form

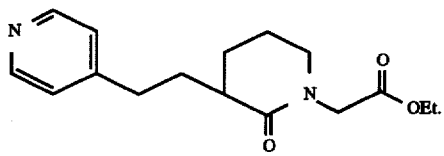
(iv-a)

The process provides an efficient and chromatography-free means for introducing the piperidinyl or pyridinyl portion of compounds described in U.S. Pat. No. 5,281,585 to the lactam portion of those compounds.

Suitable starting materials

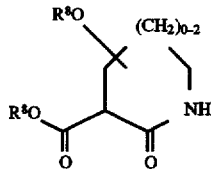

include 3-carbethoxy-2-piperidone, commercially available from Aldrich Chemical Co., Inc., (Milwaukee, Wis.), and 3-carbethoxy-2-lactam derivatives prepared from 5-, 6-, and 7-membered lactams, including 2-pyrrolidinone, 2-piperidone, 2-oxohexamethyleneimine (caprolactam), all commercially available from Aldrich Chemical Co., Inc., (Milwaukee, Wis.) and from substituted 2-pyrrolidinone, 2-piperidone, 2-oxohexamethyleneimine (e.g. substituted with OH, $C_{1-3}$ alkyl, or benzyl).

iv may be saponified to form

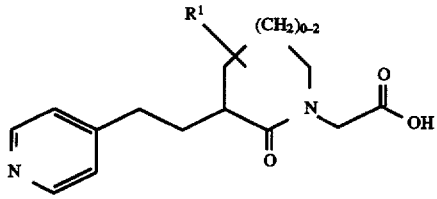

and then used to form any of a number of compounds which are useful for inhibiting the binding of fibrinogen to blood platelets. Such compounds, described in U.S. Pat. No. 5,281,585, have the general formula

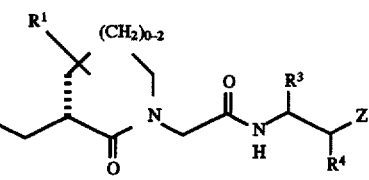

wherein
X is $R^3$ is
hydrogen,
$C_{0-6}$alkyl, either unsubstituted or substituted, with one or more groups selected from fluoro, chloro, bromo, iodo, hydroxyl, $C_{1-5}$alkylcarbonyl($C_{0-8}$alkyl)amino, aryl$C_{1-5}$alkylcarbonyl($C_{0-8}$alkyl)amino, aryloxy, $C_{1-10}$alkoxy, $C_{1-5}$alkoxycarbonyl, $C_{0-5}$alkylaminocarbonyl, $C_{1-5}$alkylcarbonyloxy, $C_{3-8}$ cycloalkyl, aryl, oxo, amino, $C_{1-6}$ alkyl, $C_{1-3}$alkylamino, amino$C_{1-3}$ alkyl, aryl$C_{0-5}$alkylaminocarbonyl, phenyl$C_{1-3}$alkylamino, aminocarbonyl$C_{0-4}$alkyl, $C_{1-8}$alkylsulfonyl($C_{0-8}$alkyl)amino, aryl $C_{0-10}$alkyl-sulfonyl($C_{0-8}$alkyl) amino, aryl$C_{0-8}$alkylsulfonyl, $C_{0-8}$alkylsulfonyl, hydroxycarbonyl$C_{0-5}$alkyl, $C_{1-8}$alkyloxycarbonyl ($C_{0-8}$alkyl)amino, aryl$C_{0-10}$alkyloxycarbonyl($C_{0-8}$alkyl)amino, $C_{0-8}$alkylaminocarbonyl($C_{0-8}$alkyl) amino, aryl$C_{0-8}$alkylaminocarbonyl($C_{0-8}$alkyl) amino, $C_{0-8}$alkylaminocarbonyloxy, aryl$C_{0-10}$alkylamino-carbonyloxy, $C_{0-8}$alkylaminosulfonyl ($C_{0-8}$alkyl)-amino, aryl$C_{0-8}$alkylaminosulfonyl($C_{0-8}$alkyl)-amino, $C_{0-8}$alkylaminosulfonyl, or aryl$C_{0-8}$ alkylaminosulfonyl; provided that the carbon atom to which $R^3$ or $R^4$ is attached bear only one heteroatom;

$R^4$ is
hydrogen,
$C_{0-6}$alkyl, either unsubstituted or substituted, with one or more groups selected from fluoro, chloro, bromo, iodo, hydroxyl, $C_{1-5}$ alkylcarbonyl($C_{0-8}$ alkyl) amino, aryl$C_{1-5}$ alkylcarbonyl($C_{0-8}$alkyl)amino, aryloxy, $C_{1-10}$alkoxy, $C_{1-5}$alkoxycarbonyl, $C_{0-5}$alkylamino-carbonyl, $C_{1-5}$alkylcarbonyloxy, $C_{3-8}$ cycloalkyl, aryl, oxo, amino, $C_{1-6}$ alkyl, $C_{1-3}$alkylamino, amino$C_{1-3}$ alkyl, aryl$C_{0-5}$alkylaminocarbonyl, phenyl$C_{1-3}$alkylamino, aminocarbonyl$C_{0-4}$alkyl, $C_{1-8}$alkylsulfonyl($C_{0-8}$alkyl)amino, aryl $C_{0-10}$alkyl-sulfonyl($C_{0-8}$alkyl) amino, aryl$C_{0-8}$alkylsulfonyl, $C_{0-8}$alkylsulfonyl, hydroxycarbonyl$C_{0-5}$alkyl, $C_{1-8}$alkyloxycarbonyl ($C_{0-8}$alkyl)amino, aryl$C_{0-10}$alkyloxycarbonyl($C_{0-8}$alkyl)amino, $C_{0-8}$alkylaminocarbonyl($C_{0-8}$alkyl) amino, aryl$C_{0-8}$alkylaminocarbonyl ($C_{0-8}$alkyl) amino, $C_{0-8}$alkylaminocarbonyloxy, aryl$C_{0-10}$alkylamino-carbonyloxy, $C_{0-8}$alkylaminosulfonyl ($C_{0-8}$alkyl)-amino, aryl$C_{0-8}$alkylaminosulfonyl($C_{0-8}$alkyl)-amino, $C_{0-8}$alkylaminosulfonyl, or aryl $C_{0-8}$alkyl-aminosulfonyl; provided that the carbon atom to which $R^3$ or $R^4$ is attached bear only one heteroatom;

Z is —CO$_2$R$^5$,

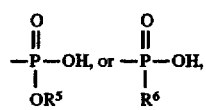

wherein

R$^6$ is C$_{1-8}$alkyl, aryl, arylC$_{1-8}$alkyl; and
R$^5$ is
  hydrogen,
  C$_{1-12}$alkyl, unsubstituted or substituted, with one or more C$_{1-6}$alkyl groups,

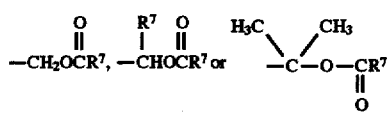

where R$^7$ is C$_{1-6}$alkyl, branched or unbranched, or phenyl, and wherein R$^7$, when appearing more than once, can be the same or different.

Hereinafter, the portion of the compound which is

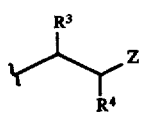

is referred to as the "amino terminal portion" of the compound.

In one class of the compounds which inhibit the binding of fibrinogen to blood platelets, the compounds have the formula

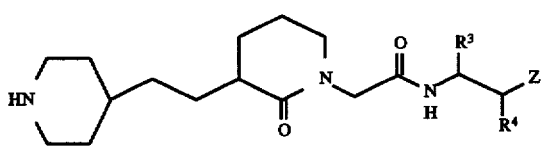

wherein

R$^3$ is hydrogen, C$_{1-6}$alkyl, arylC$_{1-6}$alkyl, or C$_{1-6}$alkyl substituted with fluoro;
R$^4$ is hydrogen; and
Z is COOH.

Exemplary compounds which may be prepared from saponified compound iv include, but are not limited to

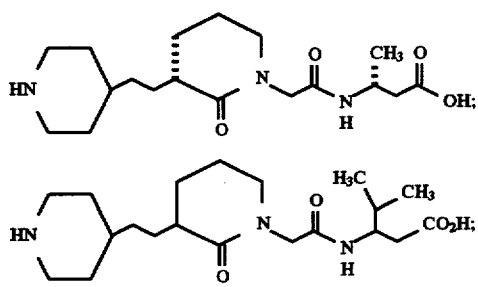

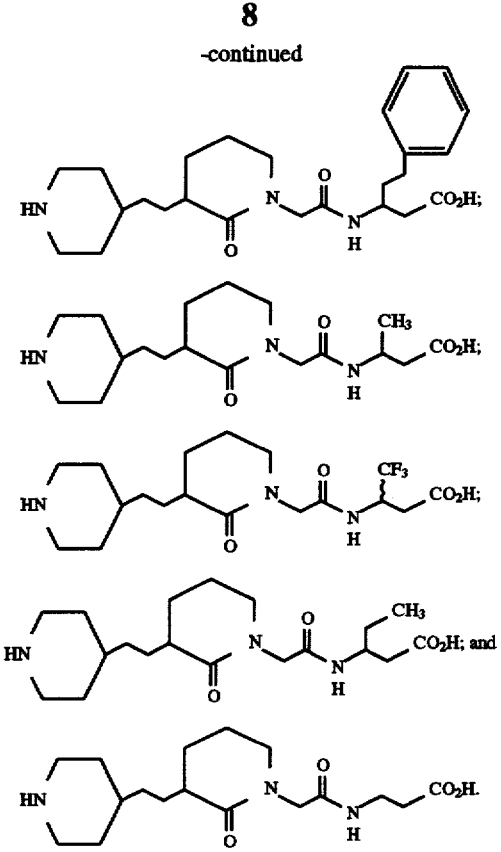

All of the above-listed compounds are active compounds as demonstrated in U.S. Pat. No. 5,281,585. The patent describes synthesis of such compounds by preparing the Boc-protected piperidinyl analog of compound iv, which is

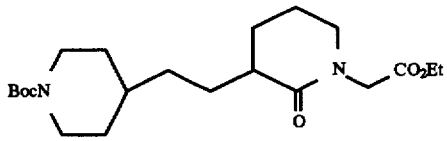

designated in column 38 as compound 49, saponifying compound 49, attaching the amino terminal portion according to procedures known in the art, and deprotecting the piperidinyl portion to produce the desired compound. U.S. Pat. No. 5,281,585 is hereby incorporated by reference for the purpose of identifying strategies known in the art for attaching the amino terminal portion to compound iv or saponified compound iv.

Fibrinogen receptor antagonists prepared with the intermediates and process of the invention may be used for inhibiting the attachment of fibrinogen to the glycoprotein IIb/IIIa receptor site. They may be administered to patients where inhibition of human or mammalian platelet aggregation or adhesion is desired.

Certain fibrinogen receptor antagonists of the invention are eliminated from circulation rapidly and are particularly useful in inhibiting platelet aggregation in situations where a strong antithrombotic of short duration or effectiveness is needed. Thus, these fibrinogen receptor antagonists may find utility in surgery on peripheral arteries (arterial grafts, carotid endaterectomy) and in cardiovascular surgery where manipulation of arteries and organs, and/or the interaction of platelets with artificial surfaces, leads to platelet aggregation and consumption. The aggregated platelets may form thrombi and thromboemboli. They may be administered to these surgical patients to prevent the formation of thrombi and thromboemboli.

The fibrinogen receptor antagonists can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount can be employed as an anti-aggregation agent.

These fibrinogen receptor antagonists may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. They may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gpIIb/IIIa on the platelet membranes and fibrinogen adsorbed to the surface of the circuit. (Gluszko et al., Amer. J. Physiol., 252(H), 615–621 (1987)). Platelets released from artificial surfaces show impaired hemostatic function. The fibrinogen receptor antagonists may be administered to prevent adhesion.

Other applications include prevention of platelet thrombosis, thromboembolism and reocclusion during and after thrombolytic therapy and prevention of platelet thrombosis, thromboembolism and reocclusion after angioplasty or coronary and other arteries and after coronary artery bypass procedures. They may also be used to prevent myocardial infarction.

The dosage regimen utilizing these fibrinogen receptor antagonists is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of these fibrinogen receptor antagonists, when used for the indicated effects, will range between about 0.01 mg per kg of body weight per day (mg/kg/day) to about 100 mg/kg/day and preferably 1.0–100 mg/kg/day and most preferably 1–20 mg/kg/day. Intravenously, the most preferred doses will range from about 1 to about 10 mg/kg/minute during a constant rate infusion. Advantageously, these fibrinogen receptor antagonists may be administered in divided doses of two, three, or four times daily. Furthermore, they can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittent throughout the dosage regime.

The fibrinogen receptor antagonists are typically administered in admixture With suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintergrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The fibrinogen receptor antagonists can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The fibrinogen receptor antagonists may also be delivered by the use of monoclonal antibodies as individual carriers to which the fibrinogen receptor antagonists are coupled. They may also be coupled with soluble polymers as targetable drag carriers. Such polymers can include polyvinlypyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, they may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The fibrinogen receptor antagonists can also be co-administered with suitable anticoagulation agents, including antiplatelet agents such as heparin, aspirin, warfarin, dipyridamole and other compounds and agents known to inhibit blood clot formation, or thrombolytic agents such as plasminogen activators or streptokinase, to achieve synergistic effects in the treatment of various vascular pathologies.

The activity of these fibrinogen receptor antagonists is illustrated below. One test used to evaluate fibrinogen receptor antagonist activity is based on evaluation of inhibition of ADP-stimulated platelets. Aggregation requires that fibrinogen bind to and occupy the platelet fibrinogen receptor site. Inhibitors of fibrinogen binding inhibit aggregation. In the ADP-stimulated platelet aggregation assay used to determine inhibition associated with these fibrinogen receptor antagonists, human platelets are isolated from fresh blood, collected into acid citrate/dextrose by differential centrifugation followed by gel filtration on Sepharose 2B in divalent ion-free Tyrode's buffer (pH 7.4) containing 2% bovine serum albumin.

Platelet aggregation is measured at 37° C. in a Chronolog aggregometer. The reaction mixture contains gel-filtered human platelets (2×10⁸ per ml), fibrinogen (100 micrograms per ml (ug/ml)), $Ca^{2+}$ (1 mM), and the fibrinogen receptor antagonists tested. The aggregation is initiated by adding 10 mM ADP 1 minute after the other components are added. The reaction is then allowed to proceed for at least 2 minutes. The extent of inhibition of aggregation is expressed as the percentage of the rate of aggregation observed in the absence of inhibitor. The $IC_{50}$ is the dose of a particular compound inhibiting aggregation by 50% relative to a control lacking the compound.

Inhibition of ADP-stimulated platelets is shown below in Table 1, which compares the concentration (dosage) of fibrinogen receptor antagonist required to inhibit aggregation by 50% relative to a control lacking the fibrinogen receptor antagonist.

TABLE 1

| Compound | IC50 µM |
|---|---|
| 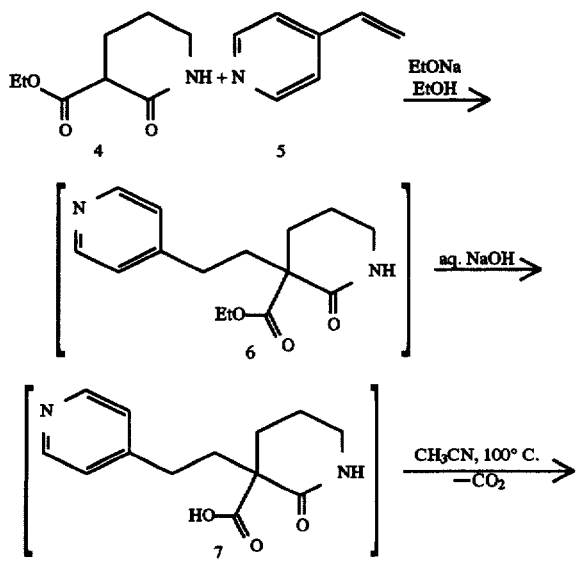 | 100 |

The following example is illustrative of the invention and should not be construed as being a limitation on the scope or spirit thereof.

EXAMPLE

Preparation of 3-[2-(Pyridin-4-yl)ethyl]-2-piperidone (3)

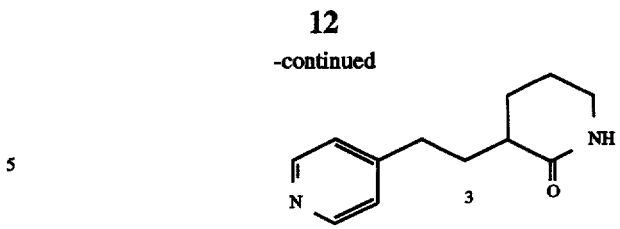

A 100 L four-necked round bottom flask equipped with a mechanical stirrer, condenser, nitrogen inlet, heating unit and a thermometer probe was purged with nitrogen overnight and then charged with 3-carbethoxy-2-piperidone (7.512 kg; 43.879 mol), anhydrous ethanol (34.1 L), 21 wt % NaOEt in EtOH (2.152 kg, 6.641 mol), 4-vinylpyridine (4.924 kg, 46.833 mol) and hydroquinone (15.0 g, 0.136 mol). The mixture was heated to 75°±2° C. for 7 h under nitrogen.

The reaction was monitored by HPLC. A sample (50 mL) of the reaction mixture was diluted to 50 mL with 50:50 $H_2O$/MeCN and then assayed.

The reaction mixture was cooled to 5°–10° C., and the saponification was initiated by the addition of cold (~10° C.) 3N aqueous NaOH (19.7 L, 59.10 mol) at such a rate that the internal temperature is did not rise higher than 25° C. The mixture was stirred for 15 h at ambient temperature (23° C.).

The mixture was cooled to 10° C. and adjusted to pH 4.7 by the addition of 12N HCl (~5.5 L). Most of the water was then distilled using steam (internal temperature at ~15° C.) under high vacuum until the solution became heterogeneous (40 L removed). Acetonitrile (37.5 L) was then added and heated to reflux (~76° C.) for 15 h to effect the decarboxylation. The mixture was cooled to ambient temperature and solid sodium bicarbonate (1.4 kg) was added. After stirring for 15 min, the two layers were separated. The aqueous layer was adjusted to pH 8.5 by the addition of 3N NaOH (~250 mL), and then extracted with acetonitrile (2×5 L).

Isopropyl acetate (12 L) was then added to the combined acetonitrile extracts which after stirring for several minutes resulted in two layers. The bottom aqueous layer (2.5 L) was removed, adjusted to pH 8.5 (from pH 7.5) by the addition of 3N NaOH and extracted with acetonitrile (3×1 L).

The combined acetonitrile extracts were dried by azeotropic distillation (~60° C., 380 mm Hg) with more acetonitrile (~40 L). After a total of 60 L distilled out, the residual water left in the mixture (KF=7 mg/mL) was removed by the addition of $Na_2SO_4$ (2 kg). This mixtue was filtered through a medium porosity funnel and the filtrate was concentrated under high vacuum (125 mm Hg) at ~45° C. After distilling out 40 L, toluene (24 L) was added and the distillation was continued. When 6 L was distilled, the mixture became heterogeneous and the distillation was stopped. To the resulting slurry was added EtOAc (5.6 L), heated to 55° C., filtered hot through $Na_2SO_4$ (2.5 kg) and 60 µm silica gel (2.5 kg) and washed with hot (50° C.) toluene/EtOAc (17 L/5.5 L). The filtrate (40 L) was concentrated by distillation using high vacuum and steam heating. After 25 L was distilled, the solid began to precipitate and the distillation was terminated. The resulting solid slurry was recrystallized by adding EtOAc (7 L) and heating to 55° C., then slowly adding hexane (12 L) and stirring at ambient temperature for 15 h under nitrogen. The crystalline solid was collected on a filter funnel and washed with EtOAc/hexane (3 L/11 L).

After vacuum-drying under nitrogen, 6.95 kg (77%) of 3-[2-(pyridin-4-yl)ethyl]-2-piperidone (3) was obtained as a tan solid (99 wt % purity, KF=1.2 mol %).

mp 84°–86° C. MS(EI) m/z 205 (MH+)

$^1$H NMR (CDCl$_3$) δ 1.60 (m, 1H), 1.76 (m, 2H), 1.85–2.10 (m, 2H), 2.29 (m, 2H), 2.73 (m, 2H), 3.31 (m, 2H), 6.05 (brs, —NH), 7.15 (d, J=6.0 Hz, 2H), 8.49 (d, J=6.0 Hz, 2H). $^{13}$C NMR (CDCl$_3$) δ 17.1, 22.1, 27.8, 28.2, 36.0, 37.9, 119.6, 145.4, 146.6, 170.2. Anal. Calcd for C$_{12}$H$_{16}$ON$_2$: C, 70.56; H, 7.90; N, 13.71. Found: C, 70.36; H, 8.17; N, 13.68.

Preparation of Ethyl [3-[2-(Pyridin-4-yl)ethyl]-2-piperidon-1-yl] acetate (10)

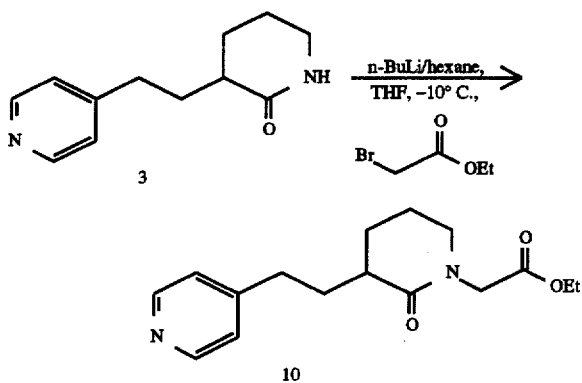

A 100 L four-necked reactor equipped with a mechanical stirrer, nitrogen inlet, cooling unit and a thermometer probe was purged with nitrogen overnight and then charged with 3-[2-(pyridin-4-yl)ethyl]-2-piperidone (3) (3.400 kg, 16.645 mol) and dry THF (34 L) and then cooled to −10°±5° C. A solution of n-butyllithium (2.5M in hexane, 6.86 L, 17.144 mol) was then added dropwise over a 2.0–2.5 h period. The mixture was allowed to warm to −5°–0° C. and then aged at this temperature for 30 min.

Ethyl bromoacetate (2.947 kg, 17.644 mol) was added as quickly as possible (~1–2 min) to the well-stirred mixture at −20° C. while maintaining the internal temperature not higher than 5° C. The mixture was allowed to warm to −5°–0° C. and then aged at this temperature for a 1 h period.

While maintaining the temperature at −10° C., the reaction was quenched by the addition of 2M aqueous sulfuric acid (16.645 L).

Hexane (16.65 L) was added and the organic layer is removed. The aqueous layer was washed with isopropyl acetate (2×8.5 L).

The aqueous solution was cooled to 10° C. and toluene (17 L) added. The pH of the rapidly stirred mixture was adjusted to 8.5–9.0 by the dropwise addition of 5M aqueous sodium hydroxide (ca. 13.3 L). The layers were separated. The aqueous was extracted with toluene (2×10 L). Each toluene extract was dried with sodium sulfate (1 kg, 0.5 kg and 0.5 kg respectively) and then filtered through sodium sulfate (1.5 kg)/silica gel 60 (1.5 kg).

The silica bed was washed with toluene (5 L). The combined filtrate was concentrated in vacuo (40° C., 100 mBar). The solution was flushed with isopropanol (20 L) and the volume then adjusted to 14 L with isopropanol. The solution was assayed to contain 4.35 kg (90%) of product. MS(EI) m/z 290 (M+).

$^1$H NMR (CDCl$_3$) δ 1.09 (t, J=7.1 Hz, 3H), 1.50 (m, 1H), 1.60–1.90 (m, 2H), 2.04 (m, 1H), 2.20 (m, 1H), 2.54 (m, 2H), 3.10–3.30 (m, 2H), 3.77 (A of AB, J=17.2 Hz, 1H), 4.01 (q, J=7.1 Hz, 2H), 4.03 (B of AB, J=17.2 Hz, 1H), 6.99 (d, J=6.0 Hz, 2H), 8.30 (d, K=6.0 Hz, 2H). $^{13}$C NMR (CDCl$_3$) δ 9.7, 17.3, 22.2, 27.9, 28.0, 36.2, 44.6, 44.9, 56.6, 119.5, 145.2, 146.6, 164.7, 168.2.

Pure product is an oil.

Preparation of [3-[2-(Pyridin-4-yl)ethyl]-2-piperidon-1-yl]-acetic Acid (11)

Saponification

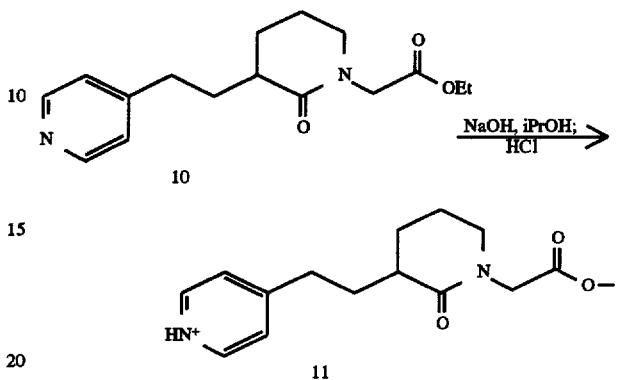

To a solution of the pyridine-ethyl ester 10 (8.700 kg, 30.000 mol) in isopropyl alcohol (26 L) was added deionized water (1.0 L) and then 49.2% aqueous sodium hydroxide (2.926 kg, 36.000 mol) at 10° C. under nitrogen over a 5 min period.

The mixture was stirred for 60 min (the reaction became homogenous) and then seeded with 20 g NaCl. The reaction mixture was quenched by slow addition of 36.4% aqueous hydrochloric acid (3.610, 36.000 mol) over a 1 h period, then diluted with isopropyl alcohol (35 L) and stirred for 30 min at ambient temperature. Most of the sodium chloride was removed by filtration through a filter funnel lined with a sheet of polypropylene and a sheet of shark skin paper. The filter cake was washed with isopropyl alcohol (2×2.5 L). The filtrate was then filtered through Solka-Floc (2 kg) to remove trace of sodium chloride. The filter cake was washed with isopropyl alcohol (2×2.5 L). The filtrate was dried by azeotropic distillation under vacuum at 30°–40° C. After distilling 50 L, 25 L isopropyl alcohol was added and then 42 L was distilled out.

Hexane (10 L) was then added over a 1 h period. After cooling to 10° C. and stirring for 1 h, the solid was collected by filtration through a filter funnel lined with a sheet of polypropylene and a sheet of shark skin paper. The product was washed with 1:1 iPrOH:hexanes (2×7 L).

After nitrogen-drying under vacuum, 6.89 kg (87%) of yellow crystalline solid was obtained.

mp 144°–145° C. MS9El) m/z 263 (MH+).

$^1$H NMR (CDCl$_3$) δ 1.70 (m, 1H), 1.80–2.05 (m, 4H), 2.20 (m, 1H), 2.40 (m, 1H), 2.78 (t, J=8.0 Hz, 2H), 3.35 (m, 1H), 3.47 (m, 1H), 3.90 (A of AB, J=17.1 Hz, 1H), 4.32 (B of AB, J=17.1 Hz, 1H), 7.27 (d, J=6.2 Hz, 2H), 8.49 (d, J=6.0 Hz, 2H). $^{13}$C NMR (CDCl$_3$) δ 17.4, 22.4, 28.1, 28.4, 36.3, 44.9, 45.1, 120.4, 142.7, 149.8, 167.7, 168.3. Anal. Calcd for C$_{14}$H$_{18}$O$_3$N$_2$: C, 64.11; H, 6.92; N, 10.68. Found: C, 64.15; H, 7.16; N, 10.66.

Preparation of [3(R)-(−)-[2-(Pyridin-4-yl)ethyl]-2-piperidon-1-yl]acetic Acid (1) via Resolution of [(±)3-[2-(Pyridin-4-yl)ethyl]-2-piperidon-1-yl]acetic Acid (11) with (S)-Methylbenzylamine

Step 1
Salt Formation and Recrystallizations

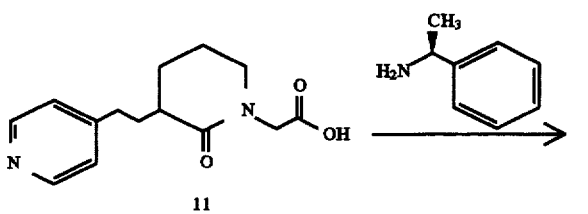

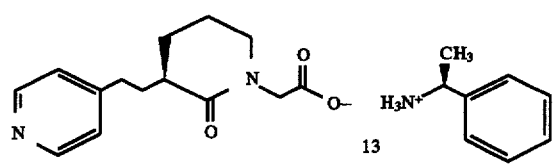

+

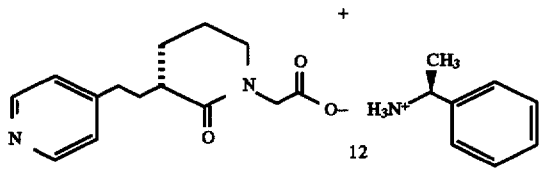

1st Crystallization (5.6 mL solvents per gram of salt)

To a suspension of acid 11 (6.787 kg, 95% pure, 24.579 mol) in isopropyl alcohol (5.55 L) and tetrahydrofuran (25.0 L) was added (S)-methylbenzylamine (3.10 kg, 98%, 25.070 mol) over a 5 min. period under a nitrogen atmosphere.

The mixture was stirred for 1 h at ambient temperature to completely dissolve the solid (took about 1 h).

The mixture was then suction-filtered through a pad of Solka-Floc (220 g, washed with THF) in a fritted funnel to remove traces of NaCl and other insolubles. The filter cake was washed with THF (2.0 L). Hexane (25.0 L) is then added slowly to the filtrate over a 1 h period. The resulting mixture is seeded with 100 mg of 99% ee salt 12. After stirring overnight at 21° C., the solid was collected on a medium porosity fritted funnel under a nitrogen blanket, washed with 3:2 THF:hexane (2×10 L) and then nitrogen-dried under vacuum for several hours to give 8.477 kg of yellow wet cake.

2nd Crystallization (7.0 mL solvents per gram salt)

The yellow wet cake was transferred to a 100 L RB flask and then isopropyl alcohol (3.3 L) and THF (14.85 L) were added. The mixture (11° C.) was heated at 45°–47° C. for 30 min to complete dissolution. Hexane (14.85 L) was then added over a 30 min period at ambient temperature. After stirring overnight at 21° C., the solid was collected on a medium porosity fritted funnel under a nitrogen blanket, washed with 3:2 THF:hexane (2×5 L) and then nitrogen-dried under vacuum for several hours to give ~7.2 kg of tan wet cake.

3rd Crystallization (6.0 mL solvents per gram salt)

The tan wet cake was transferred to a 100 L RB flask and then isopropyl alcohol (2.16 L) and THF (9.72 L) were added. The mixture (12° C.) was warmed to 25°–30° C. for 30 min. Hexane (9.72 L) was then added over a 30 min period at ambient temperature. After stirring overnight at 21° C., the solid was collected on a medium porosity fritted funnel under a nitrogen blanket, washed with 1:1 THF:hexane (2×3 L) and then nitrogen-dried under vacuum for several hours to give ~4.5 kg of tan wet cake.

4th Crystallization (6.0 mL solvents per gram salt)

The tan wet cake was transferred to a 50 L RB flask and then isopropyl alcohol (2.0 L) and THF (9.0 L) were added.

The mixture (12° C.) was warmed to 45°–48° C. and stirred at that temperature for 30 min. Hexane (9.72 L) was then added over a 30 min period at 35° C. After stirring for 64 h at 21° C., the solid was collected on a medium porosity fritted funnel under a nitrogen blanket, washed with 1:1 THF:hexane (2×3 L) and then nitrogen-dried under vacuum for several hours to give a wet tan cake.

5th Crystallization (7.5 mL solvents per gram salt)

The tan wet cake was transferred to a 50 L RB flask and then isopropyl alcohol (2.4 L) and THF (11.0 L) were added. The mixture (12° C.) was warmed to 50° C. and stirred at that temperature for 30 min. Hexane (11.0 L) was then added over a 1 h period. After stirring overnight at 21° C., the solid was collected on a medium porosity fritted funnel under a nitrogen blanket, washed with 1:1 THF:hexane (2×3 L) and then nitrogen-dried under vacuum overnight to give 3.04 kg of tan solid 12 (30% yield overall). The product was assayed by HPLC to be 99.4 wt % pure with 96.8% ee.

Step 2
Salt break and formation of zwitterionic pyridine-acid (−)-1

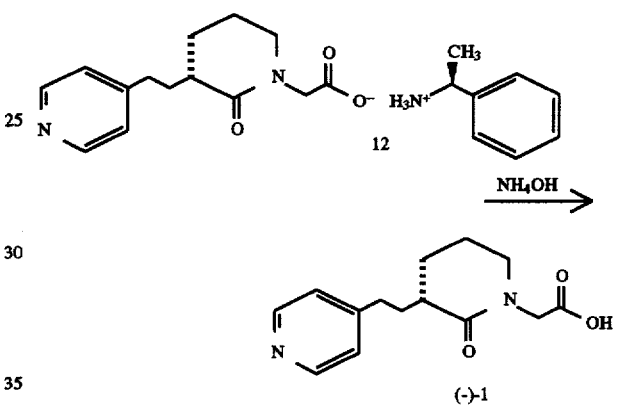

To salt 12 (2.74 kg, 7.14 mol) was added 30% ammonium hydroxide (10 L, 76.6 mol) which was then washed with toluene (4×8 L) and hexane (1×8 L).

The aqueous layer was concentrated under high vacuum (2–10 mm Hg) at 50°–60° C. to an oil and then flushed with water (2×4 L), and DMF (6×4 L) to give a beige solid. 1.852 kg was isolated, having a chemical purity of 95.6 wt % and an optical purity of 96% e.e.

Step 1
Salt break and formation of zwitterionic pyridine-acid (10)

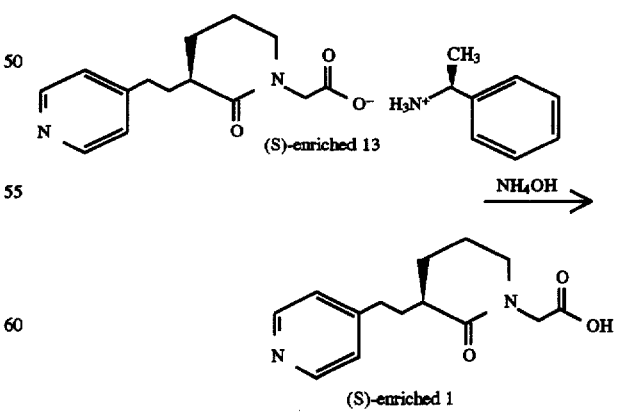

The five mother liquors from the above recrystallizations were combined and evaporated to give an oil. To this oil (~6.4 kg, ~17 mol) was added 30% ammonium hydroxide (16 L, 123.25 mol) which was washed with toluene (4×16 L) and hexane:toluene 55:45 (1×16 L). The aqueous layer was concentrated to an oil and then flushed with water (1×5 L) and isopropyl alcohol (2×5 L) to give an orange-brown oil. This oil was used directly in the next step.

Step 2

Racemization of (S)-Enriched Pyridine-Acid (1)

[Structure: (S)-enriched 1] →NaOEt/iPrOH, Δ→ [Structure: (±)-1]

To the oil (~4.25 kg, ~16.2 mol) obtained from above was added isopropyl alcohol (22 L) and solid sodium ethoxide (1.50 kg, 25.7 mol). The mixture was heated at 55°–60° C. for 3 h under nitrogen, then cooled to ambient. Concentrated HCl (2.12 L+1 L) was added until pH 4.9.

Isopropyl alcohol (22 L) was added and the resulting mixture was filtered through a 10 μm filter paper to remove sodium chloride. The filter cake was washed With isopropyl alcohol (2×5 L). The filtrate was again filtered through Solka-Floc (270 g) to remove residual sodium chloride. The filter cake was washed with isopropyl alcohol (2×1 L). The filtrate was azeotropically distilled with more isopropyl alcohol (4×10 L) until KF<1%, concentrated to about 15 L, added hexane (3 L), cooled to ~10° C. and filtered. The filter cake was washed with iPrOH:hexane 1:1 (1×4 L) and nitrogen-dried under vacuum to give 3.99 kg of yellow solid. The wt % is 89%, which is equivalent to 3.55 kg of pure racemic free acid (83%).

What is claimed is:

1. A process for preparing compounds having the formula

[Structure]

wherein

R is $C_{1-4}$ alkyl or benzyl; and $R^1$, when present, is $C_{1-4}$ alkyl, OH, O—$C_{1-4}$ alkyl, or S—$C_{1-4}$ alkyl;

which comprises a) dissolving a compound having the formula

[Structure (i)]

wherein $R^1$, when present, is $C_{1-4}$ alkyl, OH, O—$C_{1-4}$ alkyl, or S—$C_{1-4}$ alkyl; and $R^8$ is $C_{1-4}$ alkyl;

in an anhydrous alcohol solution comprising 4-vinylpyridine to form

[Structure (ii)]

b) decarboxylating the compound

[Structure (ii)]

to form

[Structure (iii)]

c) alkylating iii to form

[Structure (iv)]

2. A process according to claim 1, wherein compound iii is alkylated in the presence of a strong base.

3. A process according to claim 2, wherein the strong base is n-butyllithium.

4. A process according to claim 3, wherein i is [Structure]

ii is 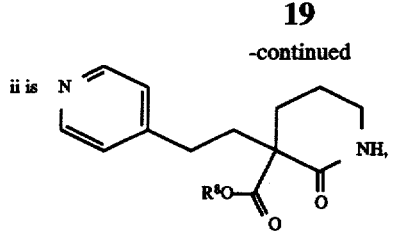
iii is 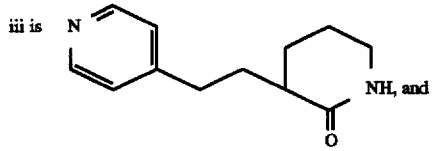
iv is 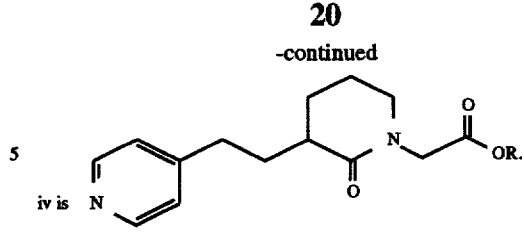
5. A process according to claim 4, wherein R is ethyl and $R^8$ is ethyl.
* * * * *